Dec. 30, 1958 R. L. BYRUM Plant Pat. 1,789
ROSE PLANT
Filed May 8, 1958
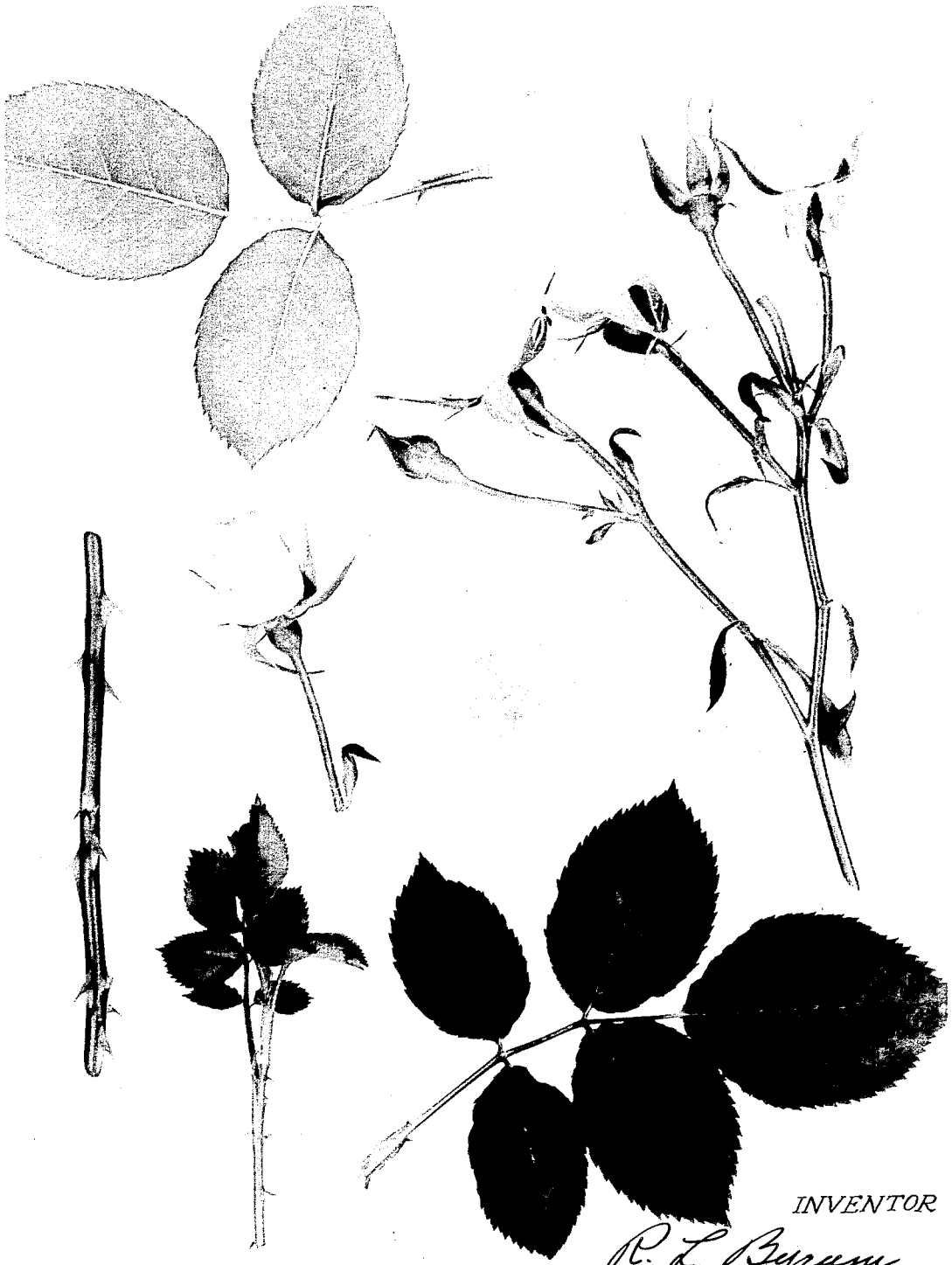
INVENTOR
R. L. Byrum
BY Robb & Robb
ATTORNEYS United States Patent Office Plant Pat. 1,789
Patented Dec. 30, 1958

1,789

ROSE PLANT

Roy L. Byrum, Richmond, Ind., assignor to Joseph H. Hill Company, Richmond, Ind., a corporation of Indiana Application May 8, 1958, Serial No. 734,066

1 Claim. (Cl. 47—61)

The present invention relates to a new and distinct variety of rose plant of the polyantha class, which was originated by me by crossing the variety "Orange Sweetheart" (Plant Patent No. 1,155) with the variety "Pinocchio" (Plant Patent No. 484).

The primary objective of this breeding was to produce a new rose variety of the "Pinocchio" type, but which has more color in the blooms. This objective was fully achieved, along with other improvements, as evidenced by the following unique combination of features which are outstanding in the new variety, and which distinguish it from its parents as well as from all other varieties of which I am aware:

(1) Vigorous "Pinocchio" type of plant growth, averaging 3 or 4 feet in height when grown in a greenhouse;

(2) Very free and unusually good flower productivity throughout each year, with prolific blooms even during the dark winter months;

(3) More blooms per cluster than are normally found in the parent variety, "Pinocchio";

(4) Good keeping quality of the flowers; and (5) An unusually good and distinctive two-tone flower color which is unique in greenhouse forcing varieties.

In comparison with the seed parent, "Orange Sweetheart," my new variety has a more free blooming habit, with more blooms per cluster, and is more productive throughout the year, and the flower color is quite different.

As compared with the pollen parent, "Pinocchio," my new variety is a more vigorous grower, and the flowers have better keeping qualities and better color.

Asexual reproduction of the new variety, by grafting, as performed at Richmond, Indiana, and also by budding, as performed at West Grove, Pennsylvania and Will's Point, Texas, shows that the aforementioned characteristics and distinctions come true to form and are established and transmitted through succeeding propagations.

The accompanying drawing shows typical specimens of the vegetative growth and flowers of my new variety, in different stages of development, and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson"), Ridgway's Color Standards and Nomenclature (hereinafter abbreviated as "Ridgway"), and Koster's Color Guide (hereinafter abbreviated as "Koster"), as indicated:

Type: Greenhouse; seedling.
Class: Polyantha.
Breeding: Seeding.
*Seed parent.*—"Orange Sweetheart."
*Pollen parent.*—"Pinocchio."
Propagation: Holds its distinguishing characteristics through succeeding propagations by both grafting and budding.

*Flower*

Locality where grown and observed: Richmond, Indiana.
Flowers borne: Several to stem; in clusters; on strong stems of medium length.
Quantity of bloom: Abundant, in greenhouse.
Continuity: Continuous.
Fragrance: Moderate. Nature—Spicy.
Bud:
*Peduncle.*—Short: small diameter; erect. Bark—smooth; color—Scheeles Green, Plate 860/2 (Wilson). Thorns—none. Prickles—numerous; color—Pure White, Plate #1 (Koster), but most have brownish tips near Maroon, Plate #97 (Koster). Hairs—none.
*Before calyx breaks.*—Size—small. Form—short pointed; ovoid; with a conspicuous neck; with foliaceous appendages on the surface of the bud; with slender, foliaceous parts extending beyond the tip of the bud equal to ¼ or more of its length. Color—Scheeles Green, Plate 860 (Wilson).
*As calyx breaks.*—Color—outside of petal—from Azalea Pink, Plate 618 (Wilson) to Azalea Pink, Plate 618/1 (Wilson).
*As first petal opens.*—Size—small. Form—short pointed; ovoid. Color: outside—Nasturtium Red, Plate 14/2 (Wilson), with base Maize Yellow Plate 607/2 (Wilson); inside—Nasturtium Red, Plate 14/2 (Wilson), lightly washed or tinted with Mandarin Red, Plate 17/2 (Wilson), and with base Aureolin, Plate 3/1 (Wilson).
*Opening.*—Opens up well in greenhouse; no unusual characteristics attributed to weather conditions.
*Size (when fully open).*—Small; from 1½ inches to 2 inches.
*Petalage.*—Semi-double; from 18 to 20 petals; arranged regularly.
*Form.*—Full at first, but becoming flat-open; petals at first being tightly rolled outward, but later becoming loosely rolled outward at maturity.
Petals:
*Texture.*—Moderately thick; leathery. Inside—satiny. Outside—satiny.
*Shape.*—Outside petals—obovate, with apex obtuse. Intermediate petals—obovate, with apex obtuse. Inside petals—obovate, with apex obtuse.

This description of a newly opened flower was made from a rose grown in a greenhouse in the month of October, at Richmond, Indiana:

*Color.*—Outer petals: outside surface—Carmine Rose, Plate 621/3 (Wilson), with Mimosa Yellow, Plate 602/1 (Wilson) at base; inside surface—Carmine Rose, Plate 621/2 (Wilson), with Mimosa Yellow, Plate 602/2 (Wilson) at base. Intermediate petals: outside surface—Nasturtium Orange, Plate 610/3 (Wilson), with Aureolin, Plate 3/2 (Wilson), at base; inside surface—Carrot Red, Plate 612/2 (Wilson), with Aureolin, Plate 3/2 (Wilson) at base. Inner petals: outside—Nasturtium Orange, Plate 610/3 (Wilson), with Aureolin, Plate 3/2 (Wilson) at base; inside surface—Carrot Red, Plate 612/2 (Wilson), with Aureolin, Plate 3/2 (Wilson) at base.

This description was made from a rose that was open for 3 days in a greenhouse in the month of October, at Richmond, Indiana:

*Color.*—Outer petals: outside surface—French Rose, Plate 520/2 (Wilson), with Aureolin, Plate 3/3 (Wilson) at base; inside surface—French Rose, Plate 520/1 (Wilson), with Aureolin, Plate 3/2 at base. Intermediate petals: outside surface—French Rose, Plate 520/3 (Wilson), with Aureolin, Plate 3/3 (Wilson) at base; inside surface—French Rose, Plate 520/2 (Wilson), with Aureolin, Plate 3/2 at base. Inner petals: outside surface—French Rose, Plate 520/3 (Wilson), with Aureolin, Plate 3/3 (Wilson) at base; inside surface—French Rose, Plate 520/2 (Wilson), with Aureolin, Plate 3/2 (Wilson) at base.

*General color effect.*—Newly opened flow—Nasturtium Red, Plate 14/2 (Wilson). 3-days open—French Rose, Plate 520/2 (Wilson).

*Behavior.*—Persist; no unusual characteristics attributed to weather conditions; fading to from Rose Pink, Plate 427/3 (Wilson) to Rose Pink, Plate 427/2 (Wilson).

*Flower longevity.*—Cut roses grown in greenhouse and kept at living-room temperatures—5 or 6 days in March.

*Reproductive organs*

Stamens: Many; arranged regularly about pistils.

Filaments: Medium length; most with anthers. Color—Aureolin, Plate 3/2 (Wilson).

Anthers: Small; all open at once. Color—Maize Yellow, Plate 607/2 (Wilson).

Pollen: Abundant. Color—Maize Yellow, Plate 607/3 (Wilson).

Pistils: Many.

Styles: Even; short; medium heavy; bunched. Color—Pure White, Plate #1 (Koster), with slight touch of Porcelain Rose, Plate 620/3 (Wilson).

Stigma: Color—Pure White, Plate #1 (Koster).

Ovularies: All encased in calyx.

Hips: None developed.

Sepals: Permanent; medium length; spear-shaped. Color: inside—Scheeles Green, Plate 860/3 (Wilson), overlaid with white fuzz; outside—Scheeles Green, Plate 860/1 (Wilson).

Seeds: None developed.

*Plant*

Foliage:

*Leaves.*—Compound of 5 to 7 leaflets; very abundant; medium large size; moderately heavy; leathery.

*Leaflets.*—Shape—oblong. Apex—acute. Base—round. Margin—simply serrate.

*Color.*—Mature: upper surface—near Empire Green, Plate XXXII (Ridgway); under surface—Deep Dull Yellow-Green (1), Plate XXXII (Ridgway). Young:

upper surface—from Scheeles Green, Plate 860/1 (Wilson) through Scheeles Green, Plate 860/2 (Wilson) and to Scheeles Green, Plate 860/3 (Wilson), with margins of Amaranth Red, Plate #43 (Koster); under surface—Scheeles Green, Plate 860/3 (Wilson), with margins of Amaranth Red, Plant #43 (Koster).

*Rachis (the supporting stem of the compound leaf.*—Medium heavy. Upper side—smooth; grooved. Under side—smooth.

*Stipules.*—Medium length; narrow; with short points turning out at an angle of more than 45°.

Growth:

*Habit.*—Bush; upright; much-branched.

*Growth.*—Free; vigorous.

*Canes.*—Medium diameter.

*Main stems.*—Color—some Spinach Green, Plate 0960 (Wilson), and some Spinach Green, Plate 0960 (Wilson), overlaid with Maroon, Plate #97 (Koster). Thorns — several; medium length; hooked downward; with short, narrow base; color—Tobacco Brown, Plate #88 (Koster) at tip, changing to Van Dyck Brown, Plate #96 (Koster) toward base. Prickles—none. Hairs—none.

*Branches.* — Color — Spinach Green, Plate #75 (Koster). Thorns — several; medium length; hooked downward; with long, narrow base; color—Lettuce Green, Plate #74 (Koster). Prickles—none. Hairs—none.

*New shoots.*—Color—Scheeles Green, Plate 860/1 (Wilson). Thorns — several; medium length; hooked downward; with long, narrow base; color—Pod Green, Plate 061/1 (Wilson), with a slight touch of Amaranth Red, Plate #43 (Koster) on top side of thorns. Prickles—none. Hairs—none.

I claim:

A new and distinct variety of rose plant of the polyantha class, substantially as herein shown and described, characterized particularly as to novelty by the unique combination of vigorous "Pinocchio" type habit of plant growth averaging 3 to 4 feet in height when grown in a greenhouse, very free and unusually good flower productivity throughout each year with prolific blooms even during the dark winter months, abundant blooms per cluster, good keeping quality of the blooms, and an unusually good and distinctive 2-tone bloom color which is unique in greenhouse forcing varieties.

No references cited.